US007519479B2

(12) United States Patent
Richardson et al.

(10) Patent No.: US 7,519,479 B2
(45) Date of Patent: Apr. 14, 2009

(54) SLOPE DETECTION FOR MEASURING GAS CONCENTRATION

(75) Inventors: Luke Edward Richardson, Calgary (CA); Peter Douglas Bush, Calgary (CA)

(73) Assignee: Galvanic Applied Sciences Inc., Calgary, Alberta (CA)

( * ) Notice: Subject to any disclaimer, the term of this patent is extended or adjusted under 35 U.S.C. 154(b) by 2 days.

(21) Appl. No.: 11/562,930

(22) Filed: Nov. 22, 2006

(65) Prior Publication Data

US 2008/0120042 A1 May 22, 2008

(51) Int. Cl.
*G01N 31/00* (2006.01)
*G06F 19/00* (2006.01)

(52) U.S. Cl. .......................................... 702/23; 702/24
(58) Field of Classification Search .................... 702/23, 702/24
See application file for complete search history.

(56) References Cited

U.S. PATENT DOCUMENTS

| 4,127,780 | A |   | 11/1978 | Kimbell ................... 250/559.1 |
|---|---|---|---|---|
| 5,047,073 | A |   | 9/1991 | Stetter et al. ...................... 95/8 |
| 5,206,519 | A |   | 4/1993 | Kirk ........................... 250/565 |
| 5,250,260 | A | * | 10/1993 | Nakano et al. ................. 422/56 |
| 5,255,074 | A |   | 10/1993 | Kimbell et al. .............. 356/445 |
| 5,542,284 | A | * | 8/1996 | Layzell et al. ................ 73/23.2 |
| 5,849,591 | A |   | 12/1998 | Bather et al. .................. 436/34 |
| 5,885,839 | A |   | 3/1999 | Lingane et al. ................ 436/34 |
| 5,952,237 | A | * | 9/1999 | Tanaka et al. ................ 436/101 |
| 6,117,686 | A | * | 9/2000 | Tanaka et al. ................ 436/167 |
| 6,319,722 | B1 |   | 11/2001 | Litwin et al. ................. 436/121 |
| 6,322,750 | B1 |   | 11/2001 | Barclay ........................ 422/56 |
| 6,947,138 | B2 | * | 9/2005 | Arno ........................... 356/437 |

OTHER PUBLICATIONS

"330 H2S Analyzer," *Envent Engineering Ltd.*, downloaded 2007, 2 pages.
"331 H2S Analyzer," *Envent Engineering Ltd.*, downloaded 2007, 2 pages.
Bush, D., "Galvanic Applied Sciences H2S Tape Analysis," 2006, 1-21.
"H2S Explosion Proof Analyzer, Continuous Tape Method," *Analytical Systems International*, 1995, 2 pages.
"Model 1000 Process Gas Analyzers," *Detcon Inc.*, downloaded 2007, 6 pages.
"Online H2S and Total Sulfur Management," *Thermo Electron Corporation*, 2001, 2 pages.
"Pipeline H2S Analysis," *Thermo Electron Corporation*, 2001, 2 pages.
"Process H2S Analyzer," *Platinum Control Technologies Corp.*, downloaded 2007, 1 page.
Richardson, L., "Analysis of Undiluted High Concentration H2S with Galvanic Applied Sciences Inc.'s 902-Series Lead Acetate Tape Analyzer," *Galvanic Applied Sciences Inc.*, 2002, 1-41.

* cited by examiner

*Primary Examiner*—Eliseo Ramos Feliciano
*Assistant Examiner*—Janet L Suglo
(74) *Attorney, Agent, or Firm*—Woodcock Washburn LLP

(57) ABSTRACT

A process and apparatus for sensing gas concentration in a gas stream involves producing a succession of difference values representing differences between successive sample values of a succession of sample values representing instantaneous reflectance of light from a compound produced by reacting a reagent with the gas being sensed and producing a gas concentration value in response to a maximum difference value of the succession of difference values.

20 Claims, 6 Drawing Sheets

SLOPE DETECTION FOR MEASURING GAS CONCENTRATION

FIELD OF THE INVENTION

This invention relates to measuring the concentration of a gas in a gas stream and more particularly to the use of slope detection in a signal representing instantaneous reflectance of light from a compound produced by reacting the gas to be detected with a reagent.

BACKGROUND OF THE INVENTION

Various methods are known for sensing gas concentration in a gas stream. For detecting hydrogen sulfide, tape analyzers are typically used. Hydrogen sulfide ($H_2S$) tape analyzers generally operate by causing a gas stream to enter a reaction chamber through an aperture and permitting the hydrogen sulfide in the gas steam to react with lead acetate on a portion of lead acetate-impregnated paper tape. As the lead acetate reacts with the $H_2S$ in the gas stream, lead sulfide is formed on the tape. As the reaction proceeds the lead sulfide build up is visible as a brown stain on the tape. Reflectance of light from the lead sulfide is measured using a photo-detector to produce a voltage signal representing instantaneous reflectance of light from the lead sulfide. After the reaction has occurred, the tape is advanced to expose a new portion of the tape in the reaction chamber.

The rate of change of the voltage signal ($dV/dt$) is proportional to the amount of $H_2S$ in the gas and the amount of lead acetate on the tape. The amount of lead acetate on the tape is generally considered to be constant in each section of the tape.

An analog to digital converter is used to produce values representing instantaneous amplitude of the voltage signal and these values are used to calculate a rate of change of the voltage signal at a particular point for use in calculating a concentration value indicating concentration of hydrogen sulfide in the gas stream.

The chemical reaction of hydrogen sulfide with lead acetate is not a linear process. When the lead acetate on the tape is initially exposed to the $H_2S$, it has no lead sulfide build up, but as the chemical reaction occurs, less and less lead acetate remains on the tape as more and more lead sulfide builds up on the tape. Initially the reaction is fast, and then it slows down. Eventually, the reaction appears to reverse because the lead sulfide build up actually becomes reflective.

Successive measurements taken by most tape analyzers vary both in the time domain and the voltage domain. A specific absolute voltage will be detected at different times for different measurements of the same gas. The voltage (or slope) measured a specific amount of time after a measurement begins will be different from measurement to measurement. Consequently $H_2S$ Tape Analyzers are typically calibrated to a single gas which has an $H_2S$ concentration that is typically about 70% of the defined full scale range of the analyzer.

Errors in measurements taken by $H_2S$ tape analyzers result from various sources including the lead-acetate impregnated tape, the constituents in the gas stream itself, the aperture size through which the gas enters the reaction chamber, temperature of the reaction chamber and sampling rate. For example, the tape used in tape analyzers has properties that can vary from measurement to measurement. The chemical properties of the paper can affect the reaction, the concentration of lead acetate on the tape may vary along the length of the tape and the temperature of the tape at the time of measurement can affect the accuracy of the measurement. Apart from temperature, it is not practical to pre-determine the properties of the tape. The paper is generally considered to be inert in the reaction, and when the tape is manufactured the lead acetate solution that the tape is dipped into is replenished, and constantly stirred so that its concentration remains generally constant along the length of the tape.

The gas stream containing the $H_2S$ gas being analyzed has many properties which can affect the accuracy of a measurement. Pressure variations can affect the flow rate, and therefore the amount of $H_2S$ passing on to the tape. Contaminants such as methyl mercaptan can cause side reactions that can affect the ability of hydrogen sulfide to react with the lead acetate.

The aperture size through which the gas stream enters the reaction chamber can also have an effect on the accuracy of a measurement. Aperture size affects the amount of gas that approaches the surface of tape and can affect the evenness with which the gas contacts the surface of the tape. This affects the repeatability as well as reaction time for any given measurement.

The temperature of the reaction chamber also affects measurements. Increasing the temperature of the reaction chamber has the effect of increasing the rate of the chemical reaction while decreasing the temperature decreases the rate of the chemical reaction. Thus a measurement taken at a higher temperature will indicate a higher gas concentration, while a measurement taken at a lower temperature will indicate a lower gas concentration.

Sampling rate can also affect the accuracy of an $H_2S$ analysis. When measuring high concentrations of $H_2S$, a low sample rate may not provide sufficient granularity in measurements for an accurate concentration value to be calculated. When measuring low concentrations with a high sample rate an excessive number of samples may be taken.

Typically, lead acetate $H_2S$ tape analyzers specify measurement error based on Full Scale. For instance, a Galvanic Applied Sciences $H_2S$ Analyzer will specify a full scale error of 1.0%. In the case of a low concentration analyzer, the full scale may be 10 PPM and a typical gas test concentration would be about 1 PPM. The Full Scale error would be 1.0% while the error on reading would be 10%.

Most $H_2S$ tape analyzers on the market today use a time-based analysis procedure to produce a concentration value. This type of analysis typically achieves an accuracy of 1.0% Standard Deviation on Full Scale.

In a time-based analysis procedure, the rate of change of voltage ($dV/dt$) produced by the photodetector is averaged over a fixed time interval beginning at a pre-defined time. For example, each measurement could involve averaging $dV/dt$ from the beginning of minute 3 to the end of minute 3. Measurements taken by this procedure are highly influenced by the effects described above and thus are neither sufficiently linear nor sufficiently repeatable for accurate, reliable measurements. Consequently, many $H_2S$ Tape Analyzer manufacturers advertise the error of measurement produced by their devices to be "Error on Full Scale" and limit the dynamic range of their analyzers.

A practical way to ensure linearity and repeatability in a time-based analysis procedure in an $H_2S$ analyzer is to reduce the dynamic range of the analyzer itself. This is done by selecting an aperture size suitable for the range of $H_2S$ concentrations being measured, calibrating with a gas close to the concentration of the gas being measured, and controlling the temperature of the reaction chamber, the incoming gas stream and/or the temperature of the tape.

Time based measurement techniques however, enable easy determination of maintenance intervals for replacement of tape cartridges.

An alternative way of measuring concentration involves a voltage-based analysis process. The voltage based analysis process is especially useful for taking measurements of gas streams having a relatively high concentration of $H_2S$. Essentially, the voltage-based process involves initiating an acquisition process when a certain threshold voltage level is detected in the signal produced by the photo detector. The acquisition process results in the acquisition of a dV/dt value acquired at a time based on the threshold voltage. The length of the time required to execute the process is typically proportional to the amount of time it takes for the reaction to produce enough lead sulfide to reflect enough light to cause the photo-detector to reach the threshold voltage.

The voltage based analysis process is based on an assumption that that the peak dV/dt occurs at roughly the same absolute voltage in the range of concentrations expected to be measured. In addition, the voltage based analysis process relies on the assumption that the peak is relatively short for high concentrations, and relatively long for low concentrations.

When compared to the timed based analysis procedure, the voltage based analysis procedure is improved in almost all respects. However, in practice measurements are only marginally better because the maximum dV/dt does not always occur at the same voltage. Thus, the analysis is non-linear and this limits the dynamic range of the technique. In short, both the time based analysis procedure and the voltage based procedure have shortcomings that need to be overcome.

SUMMARY OF THE INVENTION

In accordance with one aspect of the invention, there is provided a process for sensing gas concentration in a gas stream. The process involves producing a succession of difference values representing differences between successive sample values of a succession of sample values representing instantaneous reflectance of light from a compound produced by reacting a reagent with the gas being sensed. The process also involves producing a gas concentration value in response to a maximum difference value of the succession of difference values.

Producing the succession of difference values may involve filtering the succession of sample values to produce a succession of filtered sample values.

Filtering may involve low pass filtering the succession of sample values.

Low pass filtering may involve computing a current average value as a sum of a first fraction of a current sample value and a second fraction of a previous average value.

The first fraction may be less than the second fraction.

The first fraction may be about 0.1 and the second fraction may be about 0.9.

Producing the succession of difference values may involve computing a difference between a current sample value and a previous sample value, and storing the greater of the difference value and a previously stored difference value.

Producing the substance concentration value may involve producing the substance concentration value as a function of the maximum difference value of the succession of values.

Producing said succession of difference values may involve producing said sample values representing instantaneous reflectance of light.

Producing said sample values may involve acquiring a reference sample value.

Producing said sample values may involve sampling said signal representing instantaneous reflectance of light to produce an instantaneous sample value and subtracting said instantaneous sample value from said reference value to produce each of said succession of sample values.

In accordance with another aspect of the invention, there is provided an apparatus for measuring gas concentration in a gas stream. The apparatus includes provisions for producing a succession of difference values representing differences between successive sample values of a succession of sample values representing instantaneous reflectance of light from a compound produced by reacting a reagent with the gas being sensed. The apparatus further includes provisions for producing a gas concentration value in response to a maximum difference value of the succession of difference values.

The provisions for producing the succession of difference values may include provisions for filtering the succession of sample values to produce a succession of filtered sample values.

The provisions for filtering may include provisions for low pass filtering the succession of sample values.

The provisions for low pass filtering may include provisions for computing a current average value as a sum of a first fraction of a current sample value and a second fraction of a previous average value.

The first fraction may be less than the second fraction.

The first fraction may be about 0.1 and the second fraction may be about 0.9.

The provisions for producing the succession of difference values may include provisions for computing a difference between a current sample value and a previous sample value, and provisions for storing the greater of the difference value and a previously stored difference value.

The provisions for producing the substance concentration value may include provisions for producing the substance concentration value as a function of the maximum difference value of the succession of values.

The provisions for producing said succession of difference values may include provisions for producing said sample values representing instantaneous reflectance of light.

The provisions for producing said sample values may include provisions for acquiring a reference sample value.

The provisions for producing said sample values may include means for sampling said signal representing instantaneous reflectance of light to produce an instantaneous sample value and means for subtracting said instantaneous sample value from said reference value to produce each of said succession of sample values.

In accordance with another aspect of the invention, there is provided an apparatus for sensing gas concentration in a gas stream. The apparatus includes a receiver operably configured to receive signals representing instantaneous reflectance of light from a compound produced by reacting a reagent with the substance being sensed. The apparatus also includes a sampler operably configured to sample the signals representing instantaneous reflectance of light to produce a succession of sampled values. The apparatus further includes a processor circuit operably configured to receive the sample values, produce a succession of difference values representing differences between successive sample values of the succession of sample values, produce a gas concentration value in response to a maximum difference value of the succession of difference values, and communicate the gas concentration value to a user.

The processor circuit may be operably configured to filter the succession of sample values to produce a succession of filtered sample values.

The processor circuit may be operably configured to low pass filter the succession of sample values.

The processor circuit may be operably configured to compute a current average value as a sum of a first fraction of a current sample value and a second fraction of a previous average value.

The first fraction may be less than the second fraction.

The first fraction may be about 0.1 and the second fraction may be about 0.9.

The processor circuit may be operably configured to compute a difference between a current sample value and a previous sample value and to store the greater of the difference value and a previously stored difference value.

The processor circuit may be operably configured to produce the substance concentration value as a function of the maximum difference value of the succession of values.

The processor circuit may be operably configured to produce said sample values representing instantaneous reflectance of light.

The processor circuit may be operably configured to produce said sample values using a reference sample value.

The processor circuit may be operably configured to sample said signal representing instantaneous reflectance of light to produce an instantaneous sample value and to subtract said instantaneous sample value from said reference value to produce each of said succession of sample values.

In accordance with another aspect of the invention, there is provided a computer readable medium encoded with codes for directing a processor circuit to execute the method of claim 1.

In accordance with another aspect of the invention, there is provided a computer readable signal encoded with codes for directing a processor circuit to execute the method of claim 1.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

In drawings which illustrate embodiments of the invention.

DETAILED DESCRIPTION OF ILLUSTRATIVE EMBODIMENTS

Figure 1:
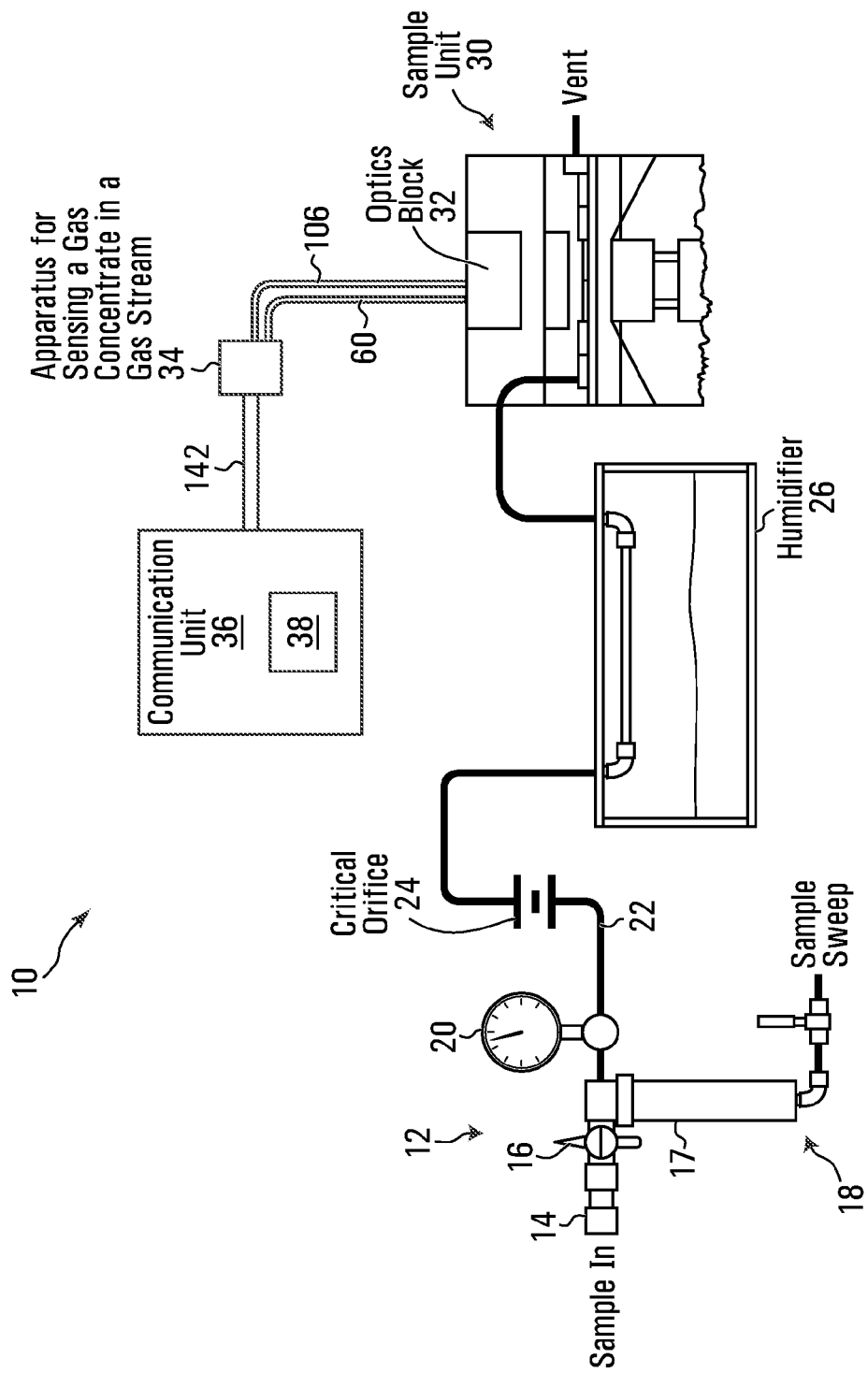
FIG. 1 is a schematic representation of a system for sensing a substance, according to a first embodiment of the invention.

Referring to FIG. 1, a system for measuring a concentration of a gas in a gas stream is shown generally at 10. The system 10 includes a gas sample system shown generally at 12, having a sample inlet 14 for receiving a gas stream from a gas source (not shown). The sample inlet 14 is in fluid communication with a valve 16 which is further in communication with a pressure regulator 17 and a flushing circuit 18 for flushing the sample system 12. The valve 16 is further in communication with a pressure gauge 20 and an outlet 22.

Essentially, the sample system 12 receives the gas stream at the sample inlet 14 and employs the valve 16 and pressure regulator 17 to cause the gas to appear at the outlet 22 at a desired pressure as indicated by the pressure gauge 20. The flushing system 18 simply allows the pressure regulator, pressure gauge and outlet 22 to be flushed free of residual gas to clean out the system 10, as desired.

The system 10 further includes a critical orifice 24 in fluid communication with the outlet 22 of the gas sample system, and a humidifier 26 in fluid communication with the critical orifice 24. The critical orifice 24 controls the rate of flow of the gas stream into the humidifier 26.

The system 10 further includes a gas sample unit 30 in fluid communication with the humidifier 26 for receiving a humidified version of the gas stream therefrom. The gas sample unit 30 facilitates reaction of a gas in the gas stream with a reagent.

The gas sample unit 30 includes an optics block 32 that shines light on a compound produced by the reaction of the gas with the reagent whereby the amount of compound produced decreases the amount of light reflected by the compound. The optics block includes a detector for detecting light reflected from the compound and produces signals representing instantaneous reflectance of light from the compound produced by the reaction. These signals representing instantaneous reflectance of light are communicated to an apparatus 34 for sensing the concentration of gas, according to one embodiment of the invention which, in response to the signals representing instantaneous reflectance of light, produces a concentration signal which is communicated to a communication unit 36 of the system. The communication unit 36 may include a display 38 for displaying a concentration value represented by the concentration signals produced by the apparatus 34. Alternatively, the communication unit 36 may communicate the concentration signals to a remote location or may include an audible device for audibly enunciating the concentration represented by the concentration signals.

In the embodiment shown, the system 10 is designed for use in detecting hydrogen sulfide ($H_2S$) concentration in the range of about 0 to 300 ppm in an undiluted natural gas stream. Thus, an inlet stream of natural gas comprising $H_2S$ in a range of 0 to 300 ppm is received at the sample inlet 14. Gas streams having $H_2S$ concentrations larger than 300 ppm may be passed through a diluter by diluting the gas stream in a stream of clean gas such as nitrogen or instrument air or any other appropriate gas. The use of diluters is generally known in the chemical arts and no further explanation is required here. The purpose of the diluter is to dilute a gas stream having a concentration of $H_2S$ greater than 300 ppm to produce a diluted gas stream in the range of 0 to 300 ppm for receipt at the sample inlet 14.

In the embodiment shown, when a natural gas steam comprising $H_2S$ having a concentration in the range of 0 to 300 ppm is received at the sample inlet, the gas stream may be received at a pressure of approximately 50 psi and reduced down to 10 psi by the pressure regulator 17. The critical orifice 24 controls the rate of gas flow into the humidifier 26 and the humidifier 26 is essentially a bubbler that exposes the gas stream to water vapour, causing the gas to be entrained with water vapour. The water vapour entrained gas stream is then received at the sample unit 30.

Sample Unit

Figure 2:
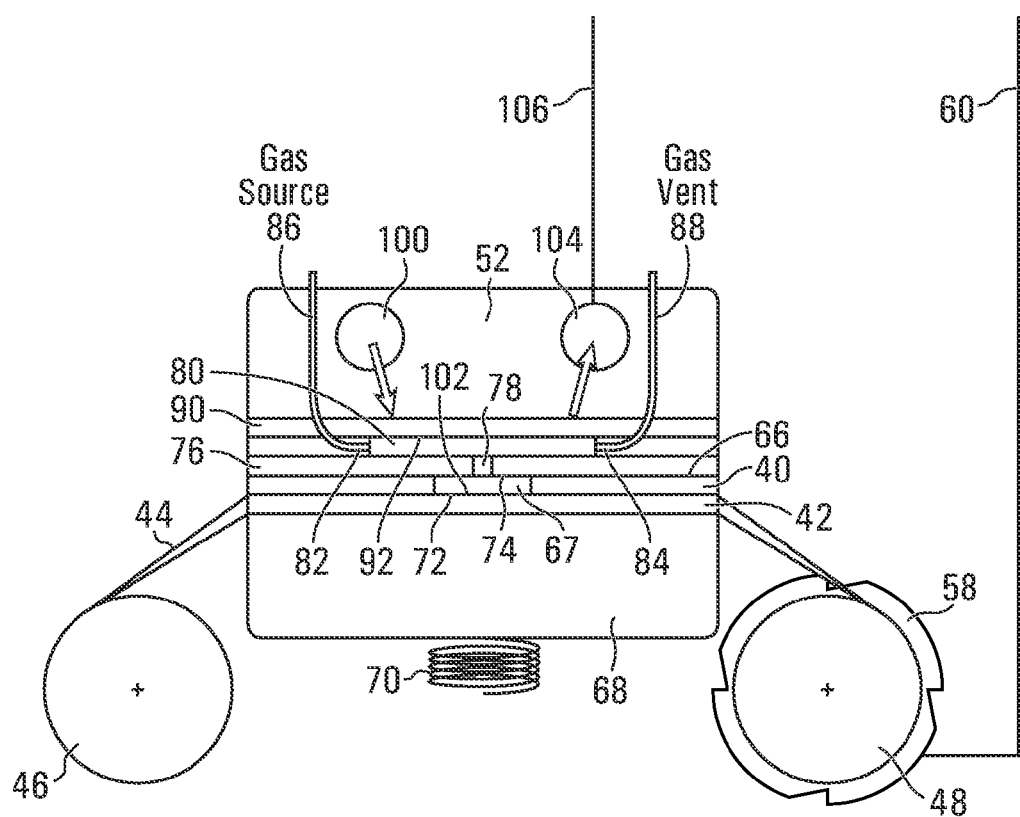
FIG. 2 is a schematic representation of a sample unit of the system shown in FIG. 1.

Referring to FIG. 2, the sample unit 30 is shown in greater detail. The sample unit 30 includes a body 40 having a rectangular recess 42 extending therethrough. The rectangular recess 42 is operable to receive a paper tape 44 treated with a solution of lead acetate. The tape 44 is wound on a supply spool 46 and is threaded through the recess 42 and is taken up on a take up spool 48. A stepper motor 58 is mechanically connected to the take up spool 48 and mechanically incrementally moves the tape through the rectangular recess 42 from the supply spool 46 to the take up spool 48, a few centimeters at a time in response to a tape advance signal received on a signal line 60 connected to the apparatus 34 shown in FIG. 1.

Referring back to FIG. 2, the body has a flat surface 66 in which is formed an opening 67 in communication with the rectangular recess 42. A Teflon® coated pressure pad 68 is connected to a compression spring 70 and urges the tape 44 tightly against the rectangular recess 42 and tightly against the opening 67 so as to seal off a bottom portion 72 of the opening 67, leaving a top portion 74 of the opening open.

The sample unit 30 further includes an inert aperture strip 76 formed of a flat piece of clear plastic, having an aperture 78 therein. The aperture 78 is located on the aperture strip 76 in such a position that when the aperture strip 76 is mounted to the flat surface 66, the aperture is aligned over the opening 67.

The body 40 further includes a gas transport chamber 80 having an inlet 82 and an outlet 84. The gas transport chamber 80 is formed such that it is in communication with the aperture 78 in the aperture strip 76. The inlet 82 to the gas transport chamber 80 is connected by a conduit 86 to the humidifier 26 shown in FIG. 1 to receive the water vapour entrained natural gas stream therefrom. The outlet 84 is connected to a gas vent through a conduit 88. A transparent seal 90 is disposed adjacent the gas transport chamber 80 and seals an external side 92 of the gas transport chamber 80, while enabling light to be received therein.

The optics block 32 is disposed adjacent the transparent seal 90 and includes a clear light source 100 which, in this embodiment, includes a clear light emitting diode (LED). The light source 100 is positioned such that light produced by the light source is received through the transparent seal 90, through the transport chamber 80, through the aperture 78, and through the opening 67 and impinges upon a surface 102 of the tape 44. The light impinging upon the surface 102 is reflected by the surface and passes back through the opening 67, through the aperture 78, through the transport chamber 80, through the transparent seal 90 and is received by a sensor 104 which produces an electrical signal representing instantaneous reflectance of light from the compound on the surface 102 of the tape 44. This electrical signal is communicated to the apparatus 34 shown in FIG. 1 by a signal line 106.

The water vapour entrained natural gas containing hydrogen sulfide is received in the conduit 86 and is communicated into the inlet 82 of the gas transport chamber 80. Some of the gas in the gas transport chamber 80 travels through the aperture 78 and into the opening 67. Since the bottom portion 72 of the opening 67 is formed by the lead acetate coated tape 44, the hydrogen sulfide in the gas stream reacts with the lead acetate to produce lead sulfide on the area of tape forming the bottom portion 72 of the opening 67. Thus, the opening 67 acts as a reaction chamber in which the hydrogen sulfide reacts with lead acetate to form a new compound—lead sulfide.

Lead acetate is a white colour whereas lead sulfide is a dark brown colour. The depth of the colour of the lead sulfide depends on the amount of lead sulfide produced, which depends upon the amount of time the lead acetate is exposed to the hydrogen sulfide. Light reflected from the tape before the tape is exposed to hydrogen sulfide is nearly equal to the light impinging upon the tape. However, as the lead sulfide builds up on the tape due to the reaction, the amount of light reflected decreases. Consequently, the voltage signal produced by the sensor 104 decreases over time as the reaction progresses. An example of this decrease is shown in FIG. 3 along with the effect of aperture size.

Figure 3:
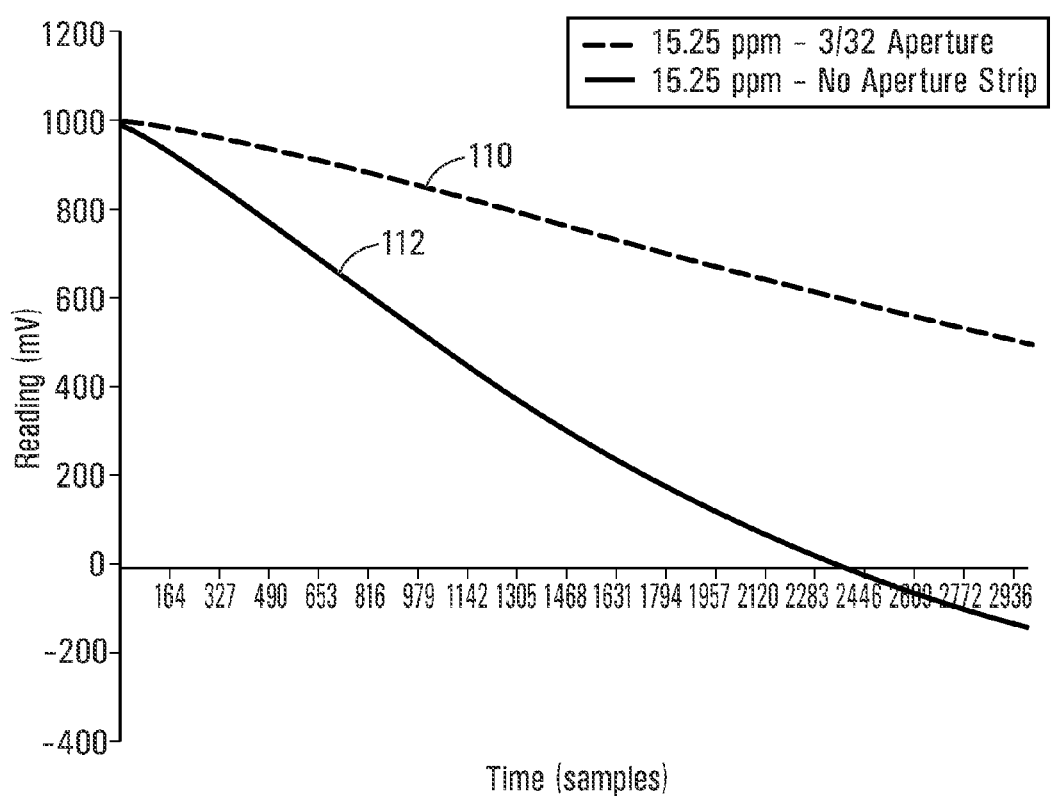
FIG. 3 is a graphical representation of signal produced by a detector of the sample unit shown in FIG. 2.

For example, FIG. 3 shows a first curve 110 illustrating a voltage signal produced by the sensor 104 shown in FIG. 2 at various times, where the gas is received in the opening 67 through a 3/32 inch aperture 78. A second curve 112 is shown to indicate the decrease in voltage over time where the hydrogen gas is at a concentration of 15.25 ppm and is received directly into the opening 67 with no aperture strip 76. From FIG. 3 it can be seen that the aperture essentially slows down the reaction because it limits the amount of $H_2S$ that can react with the lead acetate on the tape 44.

Referring back to FIG. 1, the rate of gas stream flow into the sample unit 30 is constant and thus, referring to FIG. 2, the water vapour entrained gas stream continuously flows through the gas transport chamber 80 while some of the gas stream is permitted to flow through the aperture 78 and into the opening 67 for reaction with the lead acetate on the tape 44. Since the reaction of lead acetate and hydrogen sulfide will continue until the lead acetate is consumed, the time required to consume all of the lead acetate on the tape is the maximum amount of time that the portion of the tape forming the bottom portion 72 of the recess 66 should be exposed to the hydrogen sulfide.

Consequently, as soon as a sufficient number of voltage readings has been produced by the photo detector 104, the apparatus 34 may produce a tape advancement signal which is communicated to the motor 58 on signal line 60, to cause the motor 58 to advance the tape such that a fresh portion of tape is exposed to the opening 67 and forms the bottom portion 72 thereof. As soon as the tape is advanced, a new collection of voltage readings produced by the sensor 104 can be produced. The time between successive advancements of the tape may be referred to as a cycle time, for example, where a cycle involves the production of the tape advancement signal, the advancement of the tape in response to the tape advancement signal and the collection of a plurality of voltage signals representing instantaneous reflectance of light from the compound produced by reacting lead acetate on the tape with hydrogen sulfide.

Figure 4:
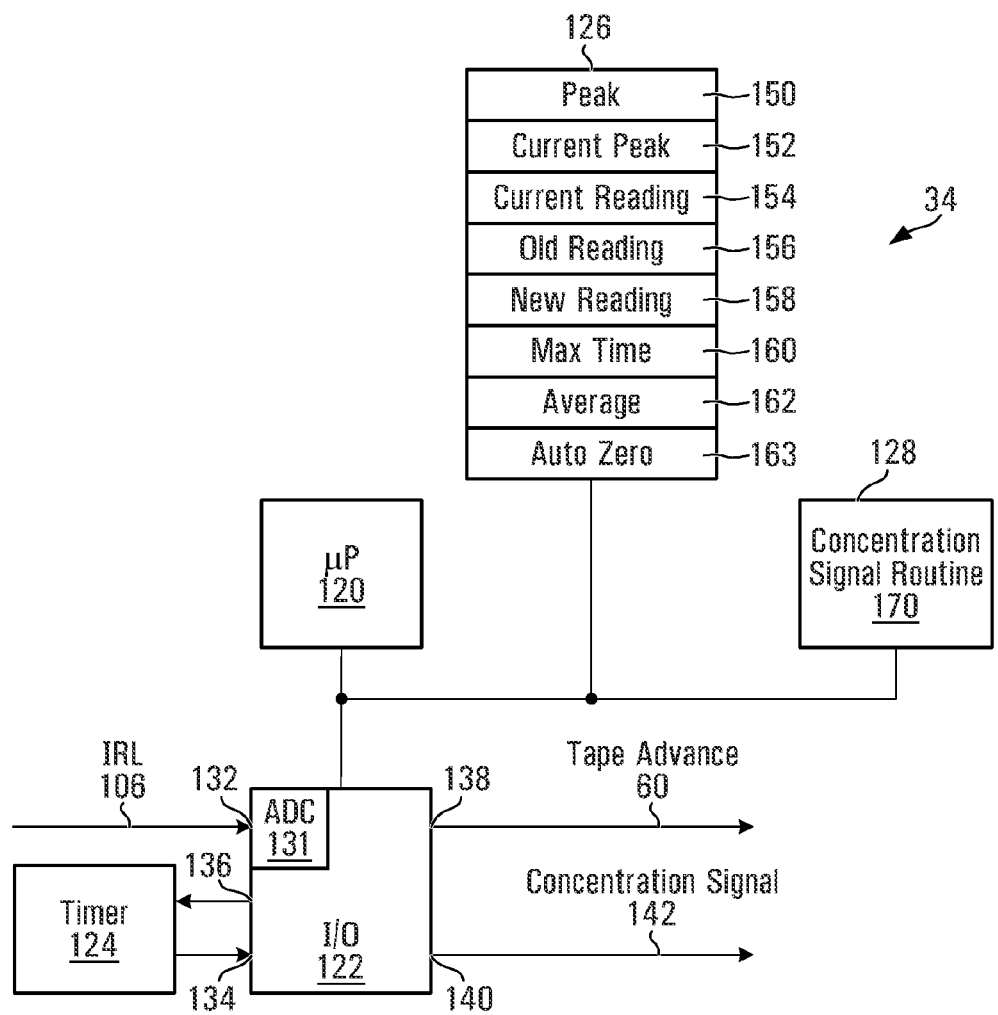
FIG. 4 is a block diagram of an apparatus for sensing a substance, of the system shown in FIG. 1, according to a first embodiment of the invention.

Referring to FIG. 4, the apparatus for sensing a gas concentration is shown in greater detail at 34. The apparatus 34 includes a processor circuit comprising a microprocessor 120, an I/O port 122, a timer 124, memory 126, and program memory 128. The I/O port 122, memory 126 and program memory 128 are all in communication with the microprocessor through a bus. The I/O port 122 has an input 132 connected to the signal line 106 for receiving the instantaneous reflected light signal from the sensor 104 shown in FIG. 2. The I/O port 122 also has a built-in analog to digital converter 131 including a sampler that converts the instantaneous reflected light signal from an analog form to a digital form.

The I/O port 122 also has an input 134 for receiving from the timer 124 a timer signal representing elapsed time. The I/O port 122 also has an output 136 for producing a timer start signal which is received at the timer 124 to cause the timer to reset and begin timing.

The I/O port 122 also includes a tape advance output 138 to which the tape advance signal line 60 is connected, for producing the tape advance signal.

The I/O port 122 also has an output 140 connected by a concentration signal line 142 to the communication unit 36 shown in FIG. 1, for communicating the concentration signal to the communication unit.

The memory 126 includes memory locations 150 through 163 for storing a peak value, a current peak value, a current reading value, an old reading value, a new reading value, a max time value, an average value, and an autozero value respectively.

The program memory 128 includes blocks of code for directing the processor circuit to carry out methods according to one aspect of the invention.

In a broad sense, the program memory 128 includes blocks of code that implement a concentration signal routine 170 that directs the processor circuit to produce a succession of difference values representing differences between successive sample values of a succession of sample values representing instantaneous reflectance of light from the compound produced by reacting a reagent (in this embodiment lead acetate) with the substance being sensed (in this embodiment hydrogen sulfide). The concentration signal routine further directs the processor circuit to produce a substance concentration value in response to a maximum difference value of the succession of difference values.

Figure 5:
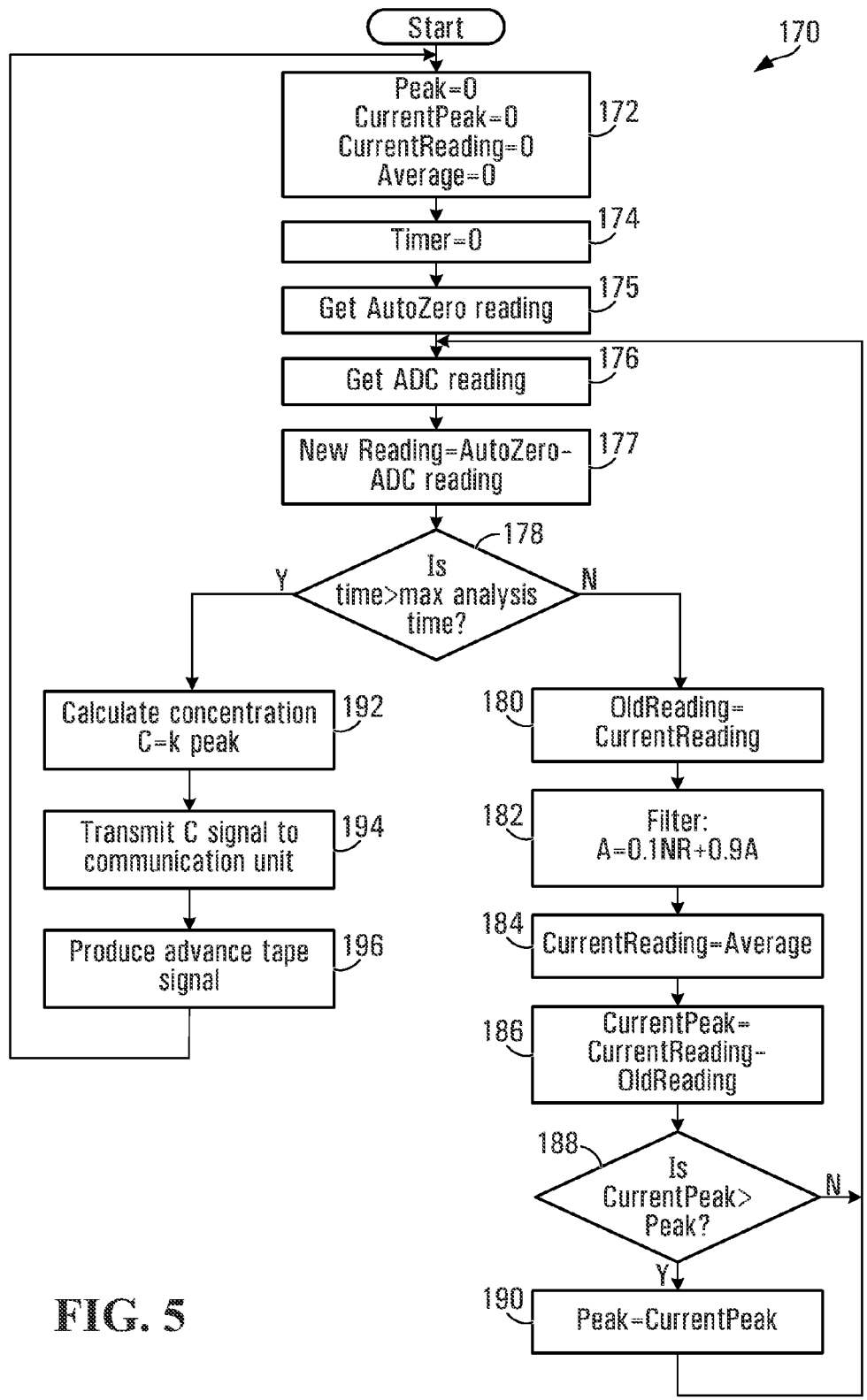
FIG. 5 is a flow chart of a concentration signal routine executed by the processor circuit shown in FIG. 4.

To do this, the concentration signal routine 170 includes a plurality of blocks of code shown best in FIG. 5. Referring to FIG. 5, the concentration signal routine is executed by the microprocessor 120 shown in FIG. 4 immediately upon powering up the microprocessor and circuit components connected thereto.

The concentration signal routine 170 includes a first block 172 that directs the processor circuit to cause the peak value, the current peak value, the current reading value, and the average value as contained in memory locations 150, 152, 154, and 162 to be set to 0 to initialize these values for later use.

Block 174 then directs the processor circuit to activate the timer output 136 to set the timer to 0 and to cause it to begin counting time.

Block 175 then directs the processor circuit to cause the I/O port 122 to actuate the analog to digital converter to cause it to take a "zero" reference sample from the instantaneous reflected light signal received at the input 132, i.e. an autozero value, and store said value in the autozero memory location 163.

Block 176 then directs the processor circuit to cause the I/O port 122 to activate the analog to digital converter 131 to cause it to take another sample value. Block 177 then directs the processor circuit to subtract the sample value acquired by the ADC from the autozero value stored in memory location 163. The resulting value may be regarded as a sample value representing instantaneous reflectance of light from the compound. This sample value is stored in the new reading memory location 158.

Block 178 then directs the processor to read the current time at the input 134, as provided by the timer signal and to compare it with the maximum time value stored in the maximum time location 160. The maximum time value may be pre-programmed to correspond to the expected time it would take at an $H_2S$ concentration of say 1 ppm, to cause the lead acetate on an exposed segment of the tape 44 shown in FIG. 2 to fully react to the point where all of the lead acetate is consumed in the reaction. A typical maximum time value may be about 600 seconds, for example.

If at block 178 it is determined that the time indicated by the timer signal is not greater than the maximum time value stored in the maximum time value location 160, the processor circuit is directed to block 180 which causes it to set the contents of the old reading memory location 156 equal to the contents of the current reading memory location 154.

The processor circuit is then directed to block 182 which causes the processor circuit to produce an average value computed as the sum of, in this embodiment, 10 percent of the contents of the new reading memory location 158 and 90 percent of an immediately previously calculated average value. The average value is then stored in average memory location 162.

Block 184 then directs the processor circuit to set the contents of the current reading memory location 154 equal to the contents of the average memory location 162.

Block 186 then directs the processor circuit to set the contents of the current peak memory location 152 equal to the difference between the contents of the current reading memory location 154 and the contents of the old reading memory location 156. This amounts to effectively taking the difference between two successive values.

Block 188 then directs the processor circuit to determine whether the contents of the current peak memory location 152 are greater than the contents of the peak memory location 150. If the contents of the current peak memory location 152 are not greater than the contents of the peak memory location 150, the processor circuit is directed back to block 176 to repeat blocks 178, 180, 182, 184, 186, and 188 to thereby acquire a succession of sample values until the contents of the current peak memory location 152 are greater than the contents of the peak memory location 150.

When the contents of the current peak memory location 152 are greater than the contents of the peak memory location 150, block 190 directs the processor circuit to set the contents of the peak memory location 150 equal to the contents of the current peak memory location 152. The processor circuit is then directed back to block 176 to continue to acquire a new sample value and re-execute blocks 178, 180, 182, 184, 186, 188, and where appropriate, block 190.

If at block 178 it is determined that the current time value indicated by the timer is greater than the contents of the maximum time location 160, the processor circuit is directed to block 192 which causes it to calculate a concentration value "C" as a function of a constant "K" and the contents of the peak memory location 150, since the contents of the peak memory location 150 represent a maximum difference value in measured instantaneous reflectance samples or in other words, the contents of the peak memory location 150 represent the maximum rate of change of voltage in time i.e. dV/dt. The $H_2S$ concentration is calculated as $H_2S$ concentration=K dv/dt.

Block 194 then directs the processor circuit to transmit the concentration signal to the communication unit 36, shown in FIG. 1, for enunciation and then block 196 directs the processor circuit to communicate with the I/O port 122 cause the tape advance signal to be produced at the output 138 for communication to the motor 58. The tape advance signal causes the motor 58 to incrementally advance the tape 44 to cause a new, unexposed portion of the tape to be positioned at the bottom portion 72 of the opening 67 shown in FIG. 2. The processor circuit is then directed to block 172 to re-execute the process described above. Thus, the concentration signal routine shown in FIG. 5, is executed once each cycle time, the cycle time being the time indicated by the maximum time value stored in the maximum time memory location 160.

In the embodiment described above, it will be appreciated that since the output of the sensor 104 is in millivolts, a signal conditioning unit (not shown) may be interposed between the sensor 104 and the analog to digital converter 131 to increase the voltage from the sensor into a range compatible with the analog to digital converter. A filter may be employed by the signal conditioning unit to smooth out the instantaneous reflectance signal. Such filter may include an analog filter, for example.

In addition, it will be appreciated that the timer 124 and/or the memory 126 and or the program memory 128 may be incorporated within the microprocessor 120 to form a single integrated unit. Alternatively, the processor circuit may be implemented in discrete logic devices (not shown) that are operably configured to implement the functionality provided by the concentration signal routine shown in FIG. 5, thereby obviating the need for the microprocessor 120.

In FIG. 5, block 182 acts to cause the processor circuit to implement a filter for filtering the succession of sample values acquired from the instantaneous reflectance signal and in the embodiment shown, filtering is achieved by calculating an average value by adding 10% of the new sample with 90% of the previously calculated average value. The weights of 10% and 90% may be varied as desired to provide for a desired amount of filtering. In any event, the average value produced by filtering may be considered to ultimately represent an instantaneous reflectance of light from the compound (lead sulfide).

Block 186 serves to cause a current difference value to be calculated, the current difference value representing a current change in reflectance since the last instantaneous reflectance value was acquired and represents a first derivative (dV/dt) of the instantaneous reflectance signal, or in other words the slope of the curve shown in FIG. 3 at a time corresponding to the time of acquisition of the current sample. Block 188 causes a comparison function that compares the current first derivate (slope) with a previously stored first derivative (slope) and block 190 serves to store the greater value of the comparison as the highest first derivative (slope) value acquired. Thus, the peak memory location 150 is updated, with the highest first derivative (slope) value observed during the cycle, until at the end of the cycle, it holds the highest first derivative (slope) value acquired during the cycle.

Figure 6:
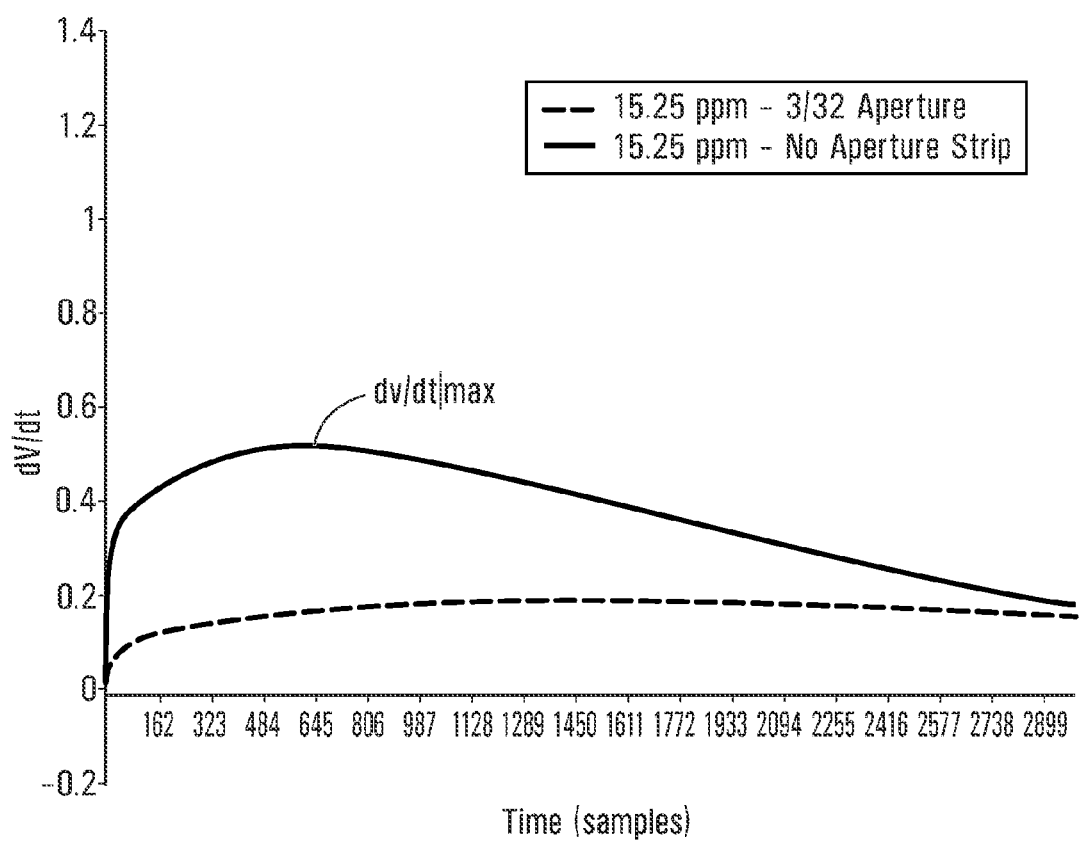
FIG. 6 is a graphical representation of a rate of change of said signal produced by the detector of the sample unit shown in FIG. 2.

An example of the trend of first derivatives (slope) of the curve shown in FIG. 3 is shown in FIG. 6. Referring to FIG. 6 it can be seen that the first derivative value (slope) of the instantaneous light reflectance signal increases to a peak and then decreases. The first derivative value (slope) at the peak represents the maximum first derivative (slope) value (dV/dt) max and is best representative of the concentration of hydrogen sulfide in the gas stream because at maximum first derivative (slope) the rate of lead sulfide buildup on the tape (44) is equal to the rate at which the chemical reaction between the hydrogen sulfide and lead acetate is creating it. Thus the maximum first derivative (slope) is proportional to the maximum concentration of hydrogen sulfide in the gas stream. Consequently, when the cycle time has been completed, the contents of the peak memory location 150 hold the maximum first derivative (slope) value and thus the value that best represents the concentration of hydrogen sulfide gas in the gas stream. Block 192 uses this maximum first derivative (slope) value to calculate a concentration value representing concentration of hydrogen sulfide gas in the gas stream.

Using the maximum first derivative (slope) to calculate the concentration value provides for excellent repeatability, providing a measurement accuracy of less than 1% of the calculated concentration value. In addition use of the maximum first derivative (slope) avoids uncertainties that can be introduced when a simple common constant time delay is used to wait until acquiring a first derivative value for use in calculating a concentration value. In addition, it will be appreciated that temperature may increase or decrease a rate of reaction, but that temperature effects will simply shift the first derivative curve left or right and this will not affect the ability of the system to find the maximum first derivative (slope) value. Consequently normal temperature variations will not affect the accuracy of the maximum first derivative (slope) value. The calculation of concentration may however be affected by temperature and therefore it would be desirable to compensate for temperature variation in the calculation of the concentration value from the maximum first derivative (slope) value or operate the sample unit in a controlled environment in which the temperature and, optionally, pressure are controlled. One aspect of temperature which is often overlooked is that the tape is stored at one temperature while the gas being analyzed is often at another temperature. One way to reduce the impact of temperature is to control the temperature of both the tape and the gas.

Finally, the above system has a wide dynamic range with high repeatability and high linearity enabling gas concentration ranges of 0 to more than 300 ppm to be measured without dilution of the gas stream.

In addition, the size of the aperture 78 will not affect the accuracy of the system and a generic calibration should work with any aperture size.

While specific embodiments of the invention have been described and illustrated, such embodiments should be considered illustrative of the invention only and not as limiting the invention as construed in accordance with the accompanying claims.

What is claimed:

1. A process for sensing gas concentration in a gas stream, the process comprising:
   producing a succession of difference values representing differences between successive sample values of a succession of sample values representing instantaneous reflectance of light from a compound produced by reacting a reagent with the gas being sensed, wherein producing said succession of difference values comprises filtering said succession of sample values to produce a succession of filtered sample values, wherein filtering comprises low pass filtering said succession of sample values by computing a current average value as a sum of a first fraction of a current sample value and a second fraction of a previous average value, and wherein said first fraction is about 0.1 and said second fraction is about 0.9; and
   producing a gas concentration value in response to a maximum difference value of said succession of difference values.

2. The process of claim 1 wherein producing the succession of difference values comprises:
   computing a difference between a current sample value and a previous sample value; and
   storing the greater of said difference value and a previously stored difference value.

3. The process of claim 1 wherein producing said gas concentration value comprises producing said gas concentration value as a function of said maximum difference value of said succession of values.

4. The process of claim 1 wherein producing said succession of difference values comprises producing said sample values representing instantaneous reflectance of light.

5. The process of claim 4 wherein producing said sample values comprises acquiring a reference sample value.

6. The process of claim 5 wherein producing said sample values comprises sampling said signal representing instantaneous reflectance of light to produce an instantaneous sample value and subtracting said instantaneous sample value from said reference value to produce each of said succession of sample values.

7. The process of claim 1 further comprising performing measurements to obtain the succession of sample values.

8. An apparatus for measuring gas concentration in a gas stream, the apparatus comprising:
    means for producing a succession of difference values representing differences between successive sample values of a succession of sample values representing instantaneous reflectance of light from a compound produced by reacting a reagent with the gas being sensed, wherein said means for producing said succession of difference values comprises means for filtering said succession of sample values to produce a succession of filtered sample values, wherein said means for filtering comprises means for low pass filtering said succession of sample values, wherein said means for low pass filtering comprises means for computing a current average value as a sum of a first fraction of a current sample value and a second fraction of a previous average value, and wherein said first fraction is about 0.1 and said second fraction is about 0.9; and
    means for producing a gas concentration value in response to a maximum difference value of said succession of difference values.

9. The apparatus of claim 8 wherein said means for producing the succession of difference values comprises:
    means for computing a difference between a current sample value and a previous sample value; and
    means for storing the greater of said difference value and a previously stored difference value.

10. The apparatus of claim 8 wherein said means for producing said gas concentration value comprises means for producing said substance concentration value as a function of said maximum difference value of said succession of values.

11. The apparatus of claim 8 wherein said means for producing said succession of difference values comprises means for producing said sample values representing instantaneous reflectance of light.

12. The apparatus of claim 11 wherein said means for producing said sample values comprises means for acquiring a reference sample value.

13. The apparatus of claim 12 wherein said means for producing said sample values comprises means for sampling said signal representing instantaneous reflectance of light to produce an instantaneous sample value and means for subtracting said instantaneous sample value from said reference value to produce each of said succession of sample values.

14. An apparatus for sensing gas concentration in a gas stream, the apparatus comprising:
    a receiver operably configured to receive signals representing instantaneous reflectance of light from a compound produced by reacting a reagent with the substance being sensed;
    a sampler operably configured to sample said signals representing instantaneous reflectance of light to produce a succession of sampled values;
    a processor circuit operably configured to:
        receive said sample values;
        produce a succession of difference values representing differences between successive sample values of said succession of sample values by low pass filtering said succession of sample values to produce a succession of filtered sample values by computing a current average value as a sum of a first fraction of a current sample value and a second fraction of a previous average value, and wherein said first fraction is about 0.1 and said second fraction is about 0.9;
        produce a gas concentration value in response to a maximum difference value of said succession of difference values; and
        communicate said gas concentration value to a user.

15. The apparatus of claim 14 wherein said processor circuit is operably configured to:
    compute a difference between a current sample value and a previous sample value; and
    store the greater of said difference value and a previously stored difference value.

16. The apparatus of claim 14 wherein said processor circuit is operably configured to produce said gas concentration value as a function of said maximum difference value of said succession of difference values.

17. The apparatus of claim 14 wherein said processor circuit is operably configured to produce said sample values representing instantaneous reflectance of light.

18. The apparatus of claim 17 wherein said processor circuit is operably configured to acquire a reference sample value for use in producing said sample values representing instantaneous reflectance of light.

19. The apparatus of claim 18 wherein said processor circuit is operably configured to sample said signal representing instantaneous reflectance of light to produce an instantaneous sample value and to subtract said instantaneous sample value from said reference value to produce each of said succession of sample values.

20. A computer readable storage medium encoded with codes that when executed on a processor cause the processor to:
    produce a succession of difference values representing differences between successive sample values of a succession of sample values representing instantaneous reflectance of light from a compound produced by reacting a reagent with the gas being sensed, wherein producing said succession of difference values comprises filtering said succession of sample values to produce a succession of filtered sample values, wherein filtering comprises low pass filtering said succession of sample values by computing a current average value as a sum of a first fraction of a current sample value and a second fraction of a previous average value, and wherein said first fraction is about 0.1 and said second fraction is about 0.9; and
    produce a gas concentration value in response to a maximum difference value of said succession of difference values.

* * * * *